(12) United States Patent
Nguyen et al.

(10) Patent No.: US 10,912,671 B2
(45) Date of Patent: Feb. 9, 2021

(54) POLYMERIC ARTICLES COMPRISING A DECORATION AND METHOD OF MANUFACTURING

(71) Applicant: LIFESTYLES HEALTHCARE PTE. LTD., Singapore (SG)

(72) Inventors: K C Nguyen, Dothan, AL (US); Beng Sim Chuah, Selangor (MY); Chayaporn Pongthanomsak, Phunphin Surat Thani (TH); Chintana Netrung, Phunphin Surat Thani (TH); Matthew Groskorth, Prahran (AU); Utain Pattanapradit, Surat Thani (TH); Paul D'Aguiar, Richmond (AU)

(73) Assignee: Lifestyles Healthcare PTE. Ltd., Singapore (SG)

( * ) Notice: Subject to any disclaimer, the term of this patent is extended or adjusted under 35 U.S.C. 154(b) by 218 days.

(21) Appl. No.: 14/055,190

(22) Filed: Oct. 16, 2013

(65) Prior Publication Data

US 2014/0109917 A1 Apr. 24, 2014

Related U.S. Application Data

(60) Provisional application No. 61/715,523, filed on Oct. 18, 2012.

(51) Int. Cl.
*A61F 6/04* (2006.01)
*B29L 31/00* (2006.01)

(52) U.S. Cl.
CPC ......... *A61F 6/04* (2013.01); *B29L 2031/7538* (2013.01)

(58) Field of Classification Search
CPC .......... A61F 2006/043; A61F 6/04–06; A41D 19/0055; A41D 19/0058
USPC ............................................ 128/844; 427/2.3
See application file for complete search history.

(56) References Cited

U.S. PATENT DOCUMENTS

| D246,117 S | 10/1977 | Okamoto | |
| 4,186,445 A * | 2/1980 | Stager | A41D 19/0068 2/164 |
| 4,553,968 A | 11/1985 | Komis | |
| 4,757,557 A * | 7/1988 | Hirano | A41D 19/0055 2/164 |

(Continued)

FOREIGN PATENT DOCUMENTS

| CN | 1760009 A | 4/2006 |
| CN | 2907583 Y | 6/2007 |

(Continued)

OTHER PUBLICATIONS

International Search Report and Written Opinion dated Jan. 22, 2014 for Application No. PCT/AU2013/001166, 10 pages.

(Continued)

*Primary Examiner* — Alireza Nia
*Assistant Examiner* — Michelle J Lee
(74) *Attorney, Agent, or Firm* — Servilla Whitney LLC

(57) ABSTRACT

Polymeric articles, such as condoms or gloves, including a decoration, are described. The polymeric article includes at least two polymeric layers, and a decoration. The decoration is at least one of a polymeric film, a decal or a temporary tattoo disposed between the at least two polymeric layers. Methods for manufacturing polymeric articles including a decoration are also described.

24 Claims, 5 Drawing Sheets

(56) References Cited

U.S. PATENT DOCUMENTS

| | | | |
|---|---|---|---|
| 5,082,004 A | 1/1992 | Reddy | |
| 5,098,755 A | 3/1992 | Tanquary et al. | |
| 5,109,871 A | 5/1992 | Thornton | |
| 5,513,654 A | 5/1996 | Delson | |
| D420,127 S | 2/2000 | Rudge et al. | |
| D434,138 S | 11/2000 | DeVries | |
| 6,170,484 B1 | 1/2001 | Feng | |
| D439,969 S | 4/2001 | Strauss et al. | |
| 6,308,708 B2 | 10/2001 | Strauss et al. | |
| 6,536,438 B1 | 3/2003 | Kakonyi | |
| 8,087,412 B2 | 1/2012 | Lucas et al. | |
| 2002/0005203 A1* | 1/2002 | Lee | A61F 6/04 128/844 |
| 2002/0189619 A1 | 12/2002 | Osterberg | |
| 2003/0124354 A1* | 7/2003 | Vistins | B29C 41/14 428/411.1 |
| 2003/0126666 A1 | 7/2003 | McNamara | |
| 2004/0105943 A1 | 6/2004 | Hoerner et al. | |
| 2008/0142021 A1* | 6/2008 | Hook | 128/844 |
| 2009/0143516 A1 | 6/2009 | MacDonald et al. | |
| 2011/0030697 A1 | 2/2011 | Thompson | |
| 2011/0041856 A1* | 2/2011 | Mistler | 128/844 |
| 2011/0203596 A1 | 8/2011 | Wang et al. | |
| 2012/0073580 A1 | 3/2012 | Chuah et al. | |
| 2012/0181726 A1 | 7/2012 | Platt et al. | |

FOREIGN PATENT DOCUMENTS

| | | | |
|---|---|---|---|
| CN | 101756759 A | 6/2010 | |
| CN | 102727337 A | 10/2012 | |
| DE | 202005000242 U1 | 5/2005 | |
| DE | 102005006019 A1 | 8/2006 | |
| EP | 0306389 A1 | 3/1989 | |
| EP | 0306389 A1 | 3/1989 | |
| EP | 0316659 A2 | 5/1989 | |
| JP | 57151329 | 9/1982 | |
| JP | 57152934 | 9/1982 | |
| JP | 61086224 | 5/1986 | |
| JP | H08215231 A | 8/1996 | |
| JP | H08215231 A | 8/1997 | |
| WO | WO-8901768 | 3/1989 | |
| WO | WO-94/02080 | 2/1994 | |
| WO | WO-97/07859 | 3/1997 | |
| WO | WO-9833459 | 8/1998 | |
| WO | WO-9926566 | 6/1999 | |
| WO | WO-02081173 A1 | 10/2002 | |
| WO | WO-2004014266 A1 | 2/2004 | |
| WO | WO 2004014266 A1 * | 2/2004 | A61F 6/04 |
| WO | WO-2006081817 A1 | 8/2006 | |
| WO | WO-2007068988 A2 | 6/2007 | |

OTHER PUBLICATIONS

International Search Report and Written Opinion dated Apr. 27, 2012 for Application No. PCT/US2011/052905, 9 pages.

International Search Report and Written Opinion dated Oct. 7, 2013 for Application No. PCT/US2013/048162, 13 pages.

Extended European Search Report dated Jun. 20, 2016 for Application No. 13846763.4.

Australian Patent Examination Report dated Jul. 19, 2016 for Patent Application No. 2013332249.

Chinese Office Action dated Jun. 1, 2017 for Application No. 201380054431.X.

* cited by examiner

POLYMERIC ARTICLES COMPRISING A DECORATION AND METHOD OF MANUFACTURING

BACKGROUND

Field

Embodiments of the present invention generally relate to polymeric articles and, more particularly, to polymeric articles comprising decorations, including multiple colors, patterns of colors, and films, and methods of fabricating such polymeric articles.

Description of the Related Art

Prophylactics and protective devices, such as gloves and condoms, which are typically made of elastomeric materials, provide physical barriers against the transmission of viruses, bacteria, chemicals, bodily and other fluids, preventing diseases and pregnancies. Typical condom designs include a shaft portion formed by a tubular sheath having an open end and a closed end. Gloves, which are also considered to be sheaths, include sheaths having tubular and non-tubular portions. Designers have attempted to create gloves and condoms having textures, patterns, and other adornments to provide different visual appearances, which may be indicia for certain properties of the device.

For example, condoms have raised features, such as studs or ribs, which are the negative of features on a condom former. Furthermore, some condoms have features, such as textures, which are produced by heat-embossing and pressure-embossing patterns onto the condom. However, condoms having these structures and methods require additional or complex manufacturing steps, additional manufacturing time, and consequently, can be prohibitively expensive as well as limited in design. Moreover, some decorations on condoms use adhesives, which can delaminate, peel, or flake off, leaving a condom with an inferior appearance as well as performance. Furthermore, such decorative features may contribute to potential medical hazards such as, for example, portions of the condom or decorations being left inside the vagina of the partner of the person wearing the condom.

Therefore, there is a need in the art for polymeric articles, for example, condoms, gloves, and the like, comprising decorations, and methods of manufacturing thereof, without the previously mentioned drawbacks.

SUMMARY

Polymeric articles comprising decorations, and methods for manufacturing such polymeric articles, substantially as shown in and/or described in connection with at least one of the figures disclosed herein, are disclosed, as set forth more completely in the claims. Various advantages, aspects, and features of the present disclosure, as well as details of an illustrated embodiment thereof, will be more fully understood from the following description and drawings.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments. It is to be understood that elements and features of one embodiment may be in other embodiments without further recitation. It is further understood that, where possible, identical reference numerals have been used to indicate comparable elements that are common to the figures.

DETAILED DESCRIPTION

Figure 1:
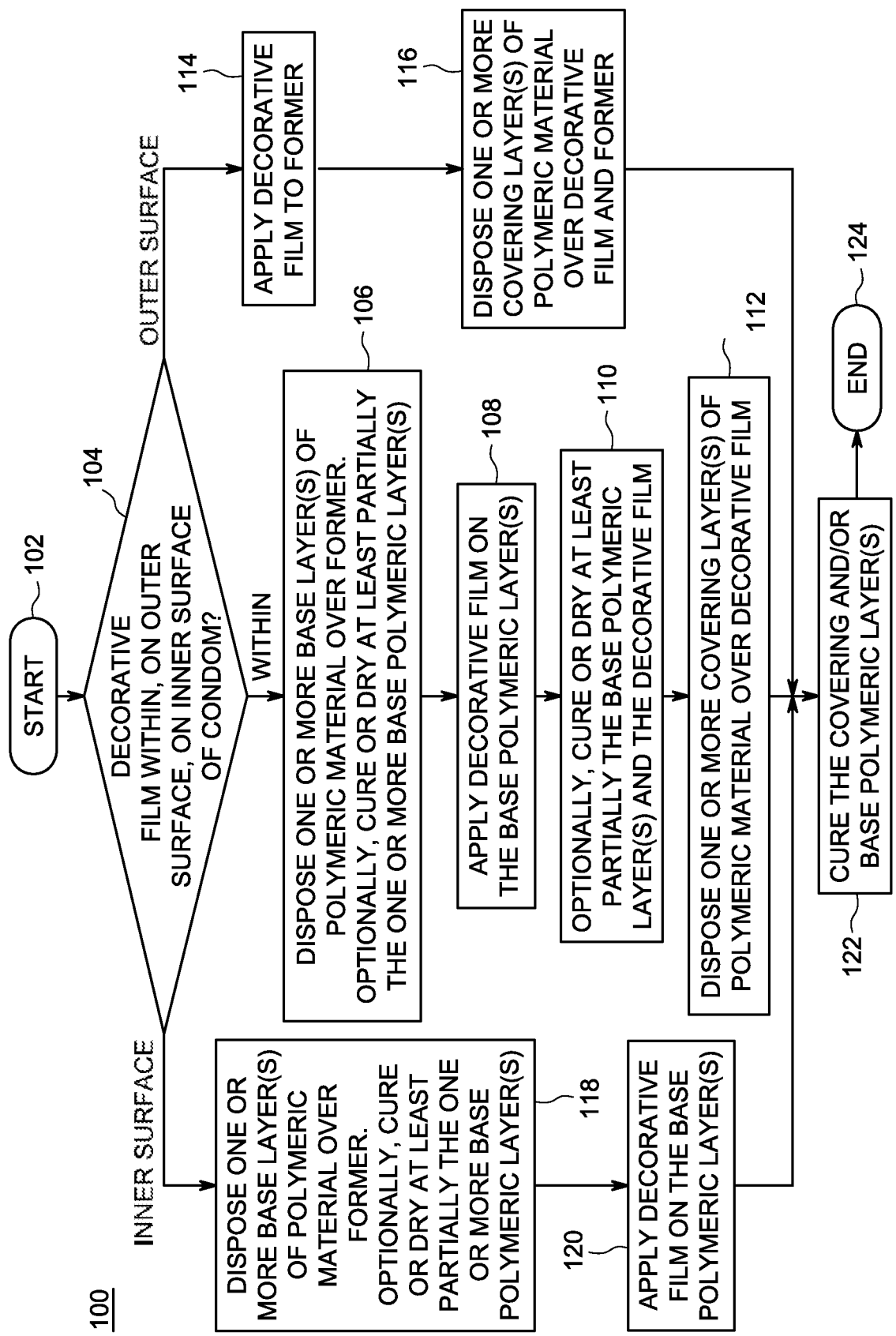
FIG. 1 depicts an illustrative method for manufacturing condoms in accordance with embodiments of the present invention.

Embodiments of the present invention pertain to polymeric articles, such as a condom or a glove having a decoration, for example, a decorative film, tattoo, decal, and the like, disposed on or embedded within the polymeric articles. In some embodiments, the article may have multiple polymeric layers, between which the decorative film is disposed. In other embodiments, a decorative film is disposed on the surface of the article, including the inner, or the outer surface, or both. In some embodiments, multiple decorations, such as decorative inks and/or films, are disposed on or within a polymeric article.

Embodiments according to the invention also comprise methods of manufacturing a polymeric article, such as a condom or a glove, having a decoration, decorative film, and/or other adornments applied thereto. In some embodiments, the decorative film comprises a polymeric film with patterns, for example, a tattoo, made using coloring materials, including inks, pigments, and the like. In some embodiments, the decorative film comprises inks that change color due to a variation in temperature, for example, thermochromic ink, inks that change color on exposure to light, for example, photochromic inks, inks that change color on application of pressure, for example, piezochromic inks, among others. According to several embodiments, the decorative patterns include visually striking features, such as the inclusion of fluorescent, glow-in-the-dark, ambient or ultraviolet light sensitive inks, photoluminescent resins, or glitter, and the like.

In one or more embodiments according to the present invention, a condom is formed from a polymeric composition that may include a rubber, elastomeric or latex material. The polymeric composition may be a synthetic rubber, natural rubber, thermoplastic elastomer, or combinations, mixtures, or blends thereof. Other examples of suitable elastomeric materials include synthetic polyisoprene, guayule, polyurethane, polyethylene, poly (vinyl chloride), nitriles, carboxylated nitriles, polychloroprene, butadienes, modified butadienes, styrene-butadienes, copolymers, block copolymers, and blends, mixtures, or combinations thereof. The term "natural rubber latex" as used herein includes cured elastomeric material sourced from *Hevea brasiliensis* (the traditional rubber tree), *Parthenum argentatum* (guayule), sunflower, goldenrod, and the like, as well as genetically modified variations of these or other biological sources. The polymeric composition, which may have a natural color or other color, may have a total solids content range from about 40 to about 70%. In some embodiments, the total solids content may be about 53%. It is to be understood that combinations of the terms polymeric, elastomeric, and latex compositions and materials may be used interchangeably.

Methods for manufacturing polymeric articles according to one or more embodiments of the invention include disposing a polymeric composition on a former, generally by a dipping process, to form an article, such as a glove, condom, or sheath, as otherwise described herein, and curing the polymeric composition disposed on the former to form a cured polymeric layer. Spraying processes for disposing elastomeric or polymeric compositions, as discussed below, are also contemplated herein. The former may be a smooth former or, alternatively, be a former having depressions on the surface, which create ribs, grooves, or studs on a surface of an article. In one or more embodiments, the former, such as for a condom, includes a tubular body having a first end and a second end. The tubular body may have an overall shape that is similar to the shape of one or more embodiments of the tubular sheath of the condom described above. The tubular body of the former may include a base segment on a first end and extends from the first end toward a second end. In one or more embodiments, the second end forms a closed end, or tip portion, of a condom, while the first end of the former is utilized to form a base portion of the condom. The tubular body of the former according to one or more embodiments may also include a middle segment that extends from the base segment toward a tip segment.

During the formation of a sheath on a former, as is known in the art, the sheath can have one or more depressions, ribs, protrusions, and textures disposed thereon as the negative of the former. The sheath can also be smooth, made from a former having no depressions, ribs, protrusions, and textures. The former may be formed from a ceramic material, metallic material, or other material known to those in the art.

In one or more embodiments of the invention, the step of disposing a polymeric composition on the former includes applying a coagulant on the former, as discussed more fully below, and dipping the former into a bath or tank containing a polymeric composition as described herein. In one or more embodiments, the former may be dipped in a bath or tank containing a polymeric composition without the use of a coagulant component. Other methods of disposing a coating or layer comprising a polymeric composition on the former may be used, such as solvent dipping or spraying.

Before disposing on a former, the temperature of the polymeric composition may be controlled, as is known in the art, and may include additives to control or modify the properties of the polymeric composition, such as the viscosity of the polymeric composition as well as the physical properties, e.g., lubricity, tensile strength, puncture resistance, and the like, of condoms formed therefrom. The polymeric composition of one or more embodiments may also include a cure package or vulcanization agents to promote cross-linking during the curing process. For example, in some embodiments, the polymeric article comprises a pre- and post-vulcanized polymeric composition, such as the technology disclosed in commonly-assigned U.S. Pat. No. 8,087,412, which is herein incorporated by reference in its entirety.

During a dipping process, as the former is dipped into the bath or tank, the dwell time and immersion and extraction speeds of the dipping process may be controlled and modified to adjust the thickness of the resulting polymeric layer that forms the, for example, glove, condom, or sheath. In one or more embodiments, the polymeric material disposed on the former is cured or otherwise treated to form a cured polymeric layer. In one or more embodiments, the polymeric layer is dried in ambient air and heated to a temperature in the range from about 50° C. to about 150° C. The resulting condom, glove, or tubular sheath replicates the shape of the former. As discussed above, in one or more embodiments, the method uses a former that includes a plurality of depressions, grooves, textures, and other features disposed on the surface thereof to form ribs, studs, or protrusions on embodiments of the condom described above.

Furthermore, color stripes and patterns may be additionally disposed on condoms using manufacturing techniques described and disclosed in commonly-assigned U.S. patent application Ser. No. 13/928,631, filed Jun. 27, 2013, which is hereby incorporated by reference in its entirety. Any of the methods for forming condoms can be used in conjunction with the methods of the present invention. In one or more embodiments, at least one method includes providing a former comprising an axial length, a circumference, and a plurality of depressions, ribs, or protrusions disposed along at least a portion of the length and around or along the circumference of the former as is disclosed in commonly assigned U.S. provisional application No. 61/385,694, filed Sep. 23, 2010; and U.S. patent application Ser. No. 13/243,038, filed Sep. 23, 2011, each of which is hereby incorporated by reference in its entirety. Embodiments of the invention can also be used in conjunction with the coloring and patterning technologies disclosed in commonly assigned U.S. Provisional application Ser. No. 13/667,770, filed Jul. 3, 2012, which is herein incorporated by reference in its entirety.

FIG. 1 depicts an illustrative method 100 for manufacturing condoms in accordance with embodiments of the present invention. Method 100 starts at step 102, and proceeds to step 104 at which point a decision is made whether to manufacture a condom having a decoration, for example, a decorative film, within the body of the condom, or on one of the surfaces of the condom, for example, an inner surface of the condom or tubular sheath intended to contact the skin of the wearer or an outer surface of the condom or tubular sheath.

If it is determined that the decorative film be disposed within the condom body of the condom, the method 100 proceeds to step 106. At step 106, polymeric material is disposed over the former forming a tubular sheath. Some embodiments according to the invention comprise a polymeric material disposed over the former in one or more layers, also referred to as the base polymeric layers. In at least one embodiment, one or more base polymeric layers may be disposed by spraying the polymeric material onto the former. In some embodiments according to the invention, the former is dipped into polymeric composition bath, such as a latex emulsion or another polymeric composition, to form a polymeric coating, i.e., a base polymeric layer, onto the former. Either of the spraying or dipping processes, or other deposition processes known in the art may be used to dispose or deposit one or more base polymeric layer(s) onto the former. Optionally, the one or more base polymeric layers disposed on the former may be allowed to dry and/or cure partially.

In some embodiments according to the invention, curing comprises placing the former with the polymeric layer disposed thereon into a heated oven while in other embodiments, the polymeric layer dries at room temperature. In one or more embodiments, the polymeric layer dries in ambient air and is subsequently heated to a temperature ranging from about 50° C. to about 150° C. In some embodiments of the invention, curing comprises heating the polymeric layer at approximately 80° C. for approximately two to three minutes. In some embodiments, the polymeric layer is cured partially, and in other embodiments, the polymeric layer is not cured at step 106. Thus, according to some embodiments, at step 106, method 100 results in a tubular sheath comprising one or more polymeric layers of polymeric composition formed over a former. As discussed above, according to various embodiments, the one or more polymeric layers may be cured, partially cured, or uncured at this stage, i.e., before a decoration is applied.

The method 100 proceeds to step 108 at which point a decoration, such as ink, pigment, or a decorative film is applied to the base polymeric layer. Specifically, the decoration is applied to the base polymeric layer of the multiple base polymeric layers. Therefore, at step 108, the tubular sheath includes the base polymeric layer or layers and the decoration disposed thereon.

A decorative film is selected from one of many known to those of ordinary skill in the art. In some embodiments of the invention, the decorative film is a tattoo, such as a temporary tattoo, or decal, as is generally known in the art. Tattoos include a decorative pattern disposed onto a substrate, such as polymeric film, paper, or a combination of polymeric film on paper, for example, by way of printing, ink-jetting, laser printing, and the like. Commercially available tattoos are generally adhered to a protective substrate layer, configured to be separated from the tattoo for use. The tattoo is released from the protective substrate, for example, by peeling the substrate layer, or by exposing the tattoo to a surface and applying a liquid, such as water, to help separate the protective substrate from the tattoo. Embodiments of the invention include wherein the decorative film, decal, or tattoo is a type of commercially available temporary tattoo on a roll or ribbon. The application of the decorative film, decal, or tattoo onto a polymeric layer is, in some embodiments according to the invention, accomplished from a roll and ribbon, transferring the decorative film, decal, or tattoo onto the polymeric layer using transfer equipment, as is discussed below. Applying decorative film to a polymeric layer, such as a tubular sheath or glove, in this manner is relatively simple, convenient, and cost effective in manufacturing a visually stimulating polymeric article.

According to several embodiments, a tattoo on a substrate is placed onto the base polymeric layer or layers, whether the base polymeric layer or layers are cured or not cured at step 106. According to some embodiments, water or another liquid is used to release the tattoo from the substrate, leaving the tattoo disposed on the base polymeric layer(s). In some embodiments, pressure is applied to the tattoo by rubbing or pressing the tattoo onto the polymeric layer to improve the adherence of the tattoo to the polymeric layer. If water or another liquid is used during the application of the decorative film onto a polymeric layer, the liquid may be dried, for example, at 80° C. for approximately one minute, or the liquid may otherwise removed before the method 100 proceeds further to optional step 110. At step 110, the sheath comprising the base polymeric layers and the decorative film is optionally cured or dried at least partially, for example as discussed earlier with respect to step 106. The method 100 then proceeds to step 112.

At step 112, polymeric material is disposed over the sheath comprising the decorative film disposed on the base polymeric layer(s) from step 110. According to several embodiments, one or more layers of polymeric material, referred to as covering polymeric layer(s), are disposed over the sheath comprising the decorative film disposed on the base polymeric layer(s). In one embodiment, the one or more covering polymeric layers may be disposed by spraying the polymeric material. In some embodiments, a polymeric composition bath, such as a latex emulsion, is utilized to form a polymeric coating, such as a covering polymeric layer(s). Either of the spraying or dipping processes, or other suitable deposition processes known in the art may be used to dispose or deposit one or more covering polymeric layer(s). Thus, at step 112, the sheath includes one or more base polymeric layers, the decorative film disposed thereon, and one or more covering polymeric layers, to provide a sheath with a decorative film disposed within the sheath of the condom.

If, at step 104, it is determined that the decorative film will be disposed on an outer surface of the condom, then the method 100 proceeds to step 114 at which point the decorative film is applied to the former. In an optional step (not shown), one or more coagulants are applied to the decorative film, before or after the decorative film is applied to the former. At step 116, polymeric material is applied over the former and the decorative film, thereby forming a sheath with a decorative film disposed on the inner surface of the sheath. According to several embodiments, one or more layers of polymeric material, referred to as covering polymeric layer(s) are disposed over the former having a decorative film disposed thereon. Thus, at step 116, the sheath includes the decorative film disposed underneath one or more covering polymeric layers.

If the decorative film will be disposed on an inner surface of the condom, then the method 100 proceeds from step 104 to step 118 at which point polymeric material is disposed over the former forming a sheath. According to some embodiments of the invention, the polymeric material is disposed over the former in one or more layers, also referred to as the base polymeric layers. The method 100 proceeds to step 120 at which point a decorative film is applied to a base polymeric layer(s). Specifically, the decorative film is applied to the last applied base polymeric layer of the multiple base polymeric layers. Thus, at step 120, the sheath includes the base polymeric layer(s) and the decorative film disposed thereon.

The method 100 proceeds from any of the steps 112, 116, or 120 to step 122, at which point the tubular sheath of the respective steps 112, 116, or 120 is cured to provide a cured condom having a decoration disposed thereon or therein. For example, the curing step 122 comprises curing in a manner similar to step 106 discussed earlier. At step 124, the method 100 ends.

In some embodiments, each and every step of the method 100 is performed. In other embodiments, some steps are omitted. In yet other embodiments, some additional steps are included, for example, steps for drying water, or for removing liquids used for separating tattoos from substrates, use of agents to aid forming of the polymeric material over the former, such as coagulants, and the like. For example, before any dipping step, either the former or a former already having a decorative film, decal, or tattoo, or an elastomeric or polymeric layer disposed thereon, may be dipped into a coagulant solution. Furthermore, in any embodiment, the decorative film, decal, or temporary tattoo may have a coagulant, as discussed below, applied thereto before it is disposed on a former or base polymeric layer to aid in adherence to the base polymeric layer or subsequent polymeric layer disposed thereon.

Also, in any embodiment of the invention, the at least one polymeric film, decal, or tattoo is unadorned. A custom image may then be applied by printing, screen-printing, ink-jetting, or laser printing on the unadorned polymeric film, decal, or tattoo after the at least one of a polymeric film, decal, or tattoo has been applied to the at least one base layer and before the at least one covering polymeric layer is disposed thereon. Moreover, a custom image may also be applied directly to the base polymeric layer by printing, screen-printing, ink-jetting, or laser printing, in any embodiment at any step in the method. A custom image in this context means applying an image of any design at the discretion of the user.

In some embodiments of the present invention, the coagulant concentration ranges from 1-50% by weight. In some embodiments of the present invention, the coagulant concentration is about 3.5 to about 5% by weight in an aqueous solution. The coagulant solution may contain Group I metal salts, Group II metal salts, or combinations thereof, and wetting agents ranging from, for example, 0.1-0.2% by weight in an aqueous solution. Coagulants include calcium nitrate, calcium citrate, calcium stearate, or other coagulants known to those in the art. In some embodiments of the invention, any of all of the polymeric layers may be cured by employing any or all of the steps of a three-step curing process by subjecting each or all of the layers by applying a strong coagulant to a former, disposing a polymeric layer thereon, applying or otherwise subjecting the polymeric layer to a weak acid, such as tricarboxylic acid, formic acid, or acetic acid, and subsequently applying a strong coagulant thereto, resulting in a stronger condom as is disclosed in commonly-assigned U.S. application Ser. No. 13/928,615, filed on Jun. 27, 2013, which is herein incorporated by reference in its entirety. Furthermore, stronger and thinner condoms can be made therewith.

In some embodiments of the invention, a coagulant may be disposed in a pattern onto any polymeric layer of a condom by spraying or dipping. A polymeric composition such as latex is subsequently thermally printed, ink-jetted, or injected onto the condom. The elastomeric or polymeric layer is built up on substantially the same pattern as the applied coagulant. In some embodiments of the present invention, ink, or pigment solutions are disposed on the condom using a silkscreening process. A silkscreen can be disposed on a tubular sheath, the tubular sheath sprayed with coagulant, and a layer of colored polymeric composition sprayed thereon, as is disclosed in commonly assigned U.S. provisional application Ser. No. 61/667,770, which is herein incorporated by reference in its entirety. In some embodiments of the present invention, a subsequent ink layer may be disposed by silkscreening, and another layer of latex disposed thereon. In some embodiments, this process is repeated several times. Also, the polymeric composition or latex emulsion may be applied by spraying via an air gun. For example, one air gun suitable for use with embodiments of the invention is a TRANSTAR AUTOBODY TECHNOLOGIES® HVLP 1.3 mm model, having a maximum pressure of 20 psi and atomizing air nozzle having a maximum pressure of 10 psi. The air gun, including the polymeric composition or latex emulsion tank, connects to the atomizing air nozzle. The polymeric composition or latex emulsion is sprayed using compressed air or nitrogen and is deposited onto a mold or onto a pattern template. The amount of latex deposited on the mold or condom depends on the air pressure used, a higher air pressure delivering more latex. A silk screen having a design image is laid over the condom and the ink, or a natural-color or colored polymeric composition having ink admixed therein, is then forced through the mesh screen in the pattern image area and disposed onto the condom. Once the pattern image is disposed onto the condom, an additional layer of a polymeric composition may be disposed thereon, sealing the image or decoration between polymeric layers, as discussed above.

Figure 2:
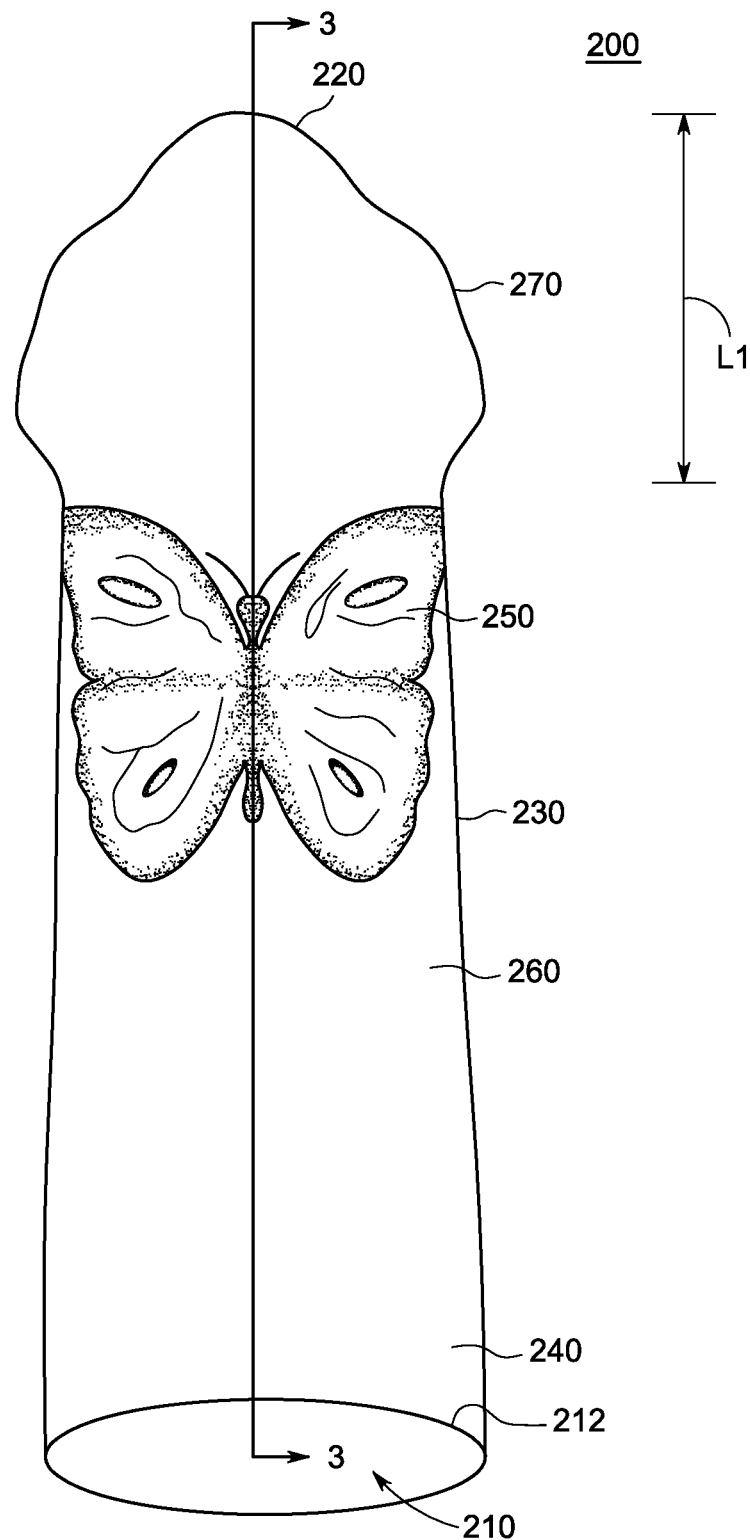
FIG. 2 depicts a condom in accordance with at least one embodiment of the invention.
Figure 3:
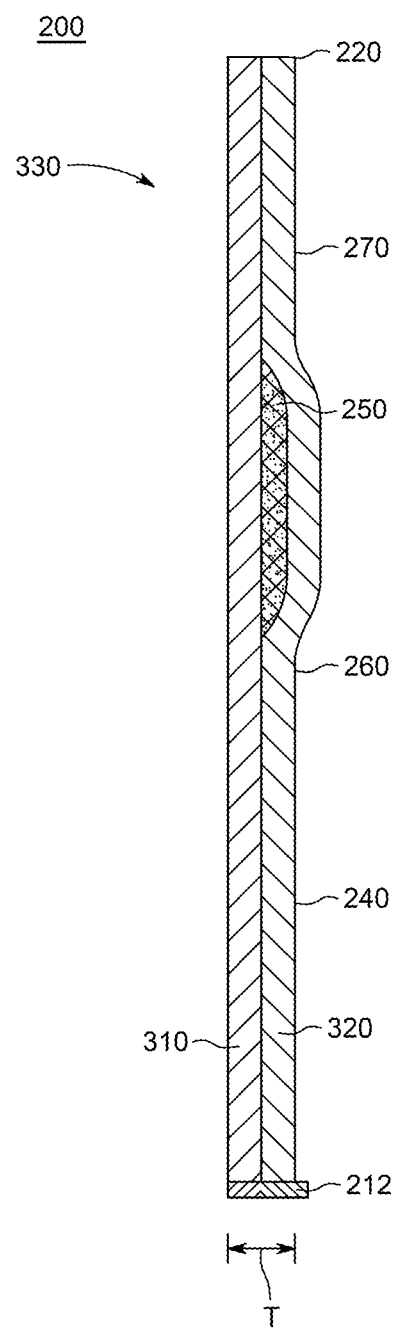
FIG. 3 depicts a cross-sectional view of the condom depicted in FIG. 2, taken along line 3-3, in accordance with at least one embodiment of the invention.
Figure 4:
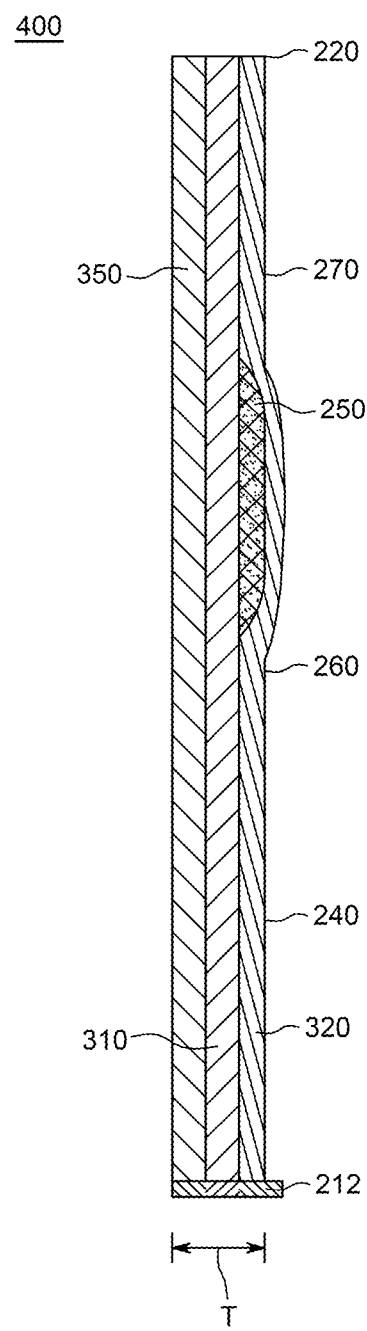
FIG. 4 depicts the cross-sectional view of FIG. 3 having an additional latex layer disposed thereon.

Embodiments of condoms according to the invention are shown in FIGS. 2-4. FIG. 2 depicts a condom 200 in accordance with at least one embodiment of the invention. Condom 200 includes an open end 210, a closed end 220, and a tubular sheath 230 extending therebetween. The tubular sheath 230 includes an axial length and a surface defining a circumference. Along tubular sheath 230 is disposed at least one decorative film, such as a decal or tattoo 250. As shown, the tattoo 250 is a butterfly, but can comprise nearly any image. As will be described below, decorative film, decal, or tattoo 250 is disposed between two polymeric layers, and is visible when viewed from the surface that is not intended to contact skin when in use. Decorative film, decal, or tattoo 250 may be made of any material compatible with latex, such as various acrylics, mylar, vinyls, such as poly (vinyl chloride), poly (vinyl alcohol), and poly (vinyl pyrrolidone), and the like.

Condom 200 may further comprise a ring 212. The ring 212 may be formed, for example, by a recessed groove in a condom former, so that ring 212 is part of one continuous structure formed when other portions of the tubular sheath 230 are formed. Tubular sheath 230 includes a base portion 240 that is disposed adjacent to open end 210 and extends from the open end 210 toward closed end 220. Tubular sheath 230 also includes a middle portion 260 extending from base portion 240 toward closed end 220. Base portion 240 and middle portion 260 have, for example, a combined length in the range from about 95 mm to about 135 mm. Alternatively, base portion 240 and middle portion 260 may have a combined length of about 120 mm. In one or more embodiments, base portion 240 may have a length that is greater than the length of middle portion 260. The base portion 240 of one or more embodiments may have a length in the range from about 90 mm to about 120 mm. In some embodiments, the length of base portion 240 may be about 105 mm. The length of middle portion 260 may be varied. Condom 200 also comprises tip portion 270, having a length L1, in the range from about 50 mm to about 70 mm. In another embodiment, tip portion 270, adapted to fit over the glans of a penis, may have a length L1 in the range from about 55 mm to about 65 mm.

FIG. 3 depicts a cross-sectional view of the condom depicted in FIG. 2, taken along line 3-3, in accordance with at least one embodiment of the invention. Condom 200 has two elastomeric or polymeric layers, a base polymeric layer 310 and a covering polymeric layer 320, for example as discussed with reference to FIG. 1. According to various embodiments, the decorative film or a tattoo 250 is disposed between layers 310 and 320 as illustrated by a cross-section 330 of the decorative film 250. The decorative film 250 may traverse the entire circumference of condom 200 or any portion thereof. In one embodiment, the decorative film 250 is disposed on the exterior surface of the covering polymeric layer 320 (not shown), and in another embodiment, the decorative film 250 is disposed on the interior surface of base polymeric layer 310 (not shown). Furthermore, according to several embodiments, the decorative film 250 is disposed within or on the condom 200 at the tip portion 270, base portion 240 or any other portion of tubular sheath 230.

In one or more embodiments, the cross-sectional thickness T of open end 210, not including the ring 212, of condom 200 may be approximately 0.05-0.25 mm. In one or more embodiments, open end 210 of condom 200 may be larger, however, it will be understood that the remaining portions of the condom may also be larger in a proportional manner as understood in the art. The cross-sectional thickness T of tubular sheath 230 may, optionally, decrease along base portion 240 and middle portion 260 from open end 210 to tip portion 270 (not shown).

FIG. 4 depicts the cross-sectional view of FIG. 3 having an additional latex layer disposed thereon. Condom 400 has an additional polymeric layer 350 or a third latex layer 350. According to some embodiments, the additional polymeric layer 350 is formed over the former, the base polymeric layer 310 is formed over the additional polymeric layer 350, the decorative film or tattoo 250 is disposed onto the base polymeric layer 310 thereafter, and the covering polymeric layer 320 is then formed over the decorative film 250 and the base polymeric layer 310. In this embodiment, the covering polymeric layer 320 is the skin-contacting layer.

In other embodiments of the invention, the base polymeric layer 310 is formed over the former, the decorative film or tattoo 250 is disposed onto the base polymeric layer 310, the covering polymeric layer 320 is then formed over the decorative film 250 and the base polymeric layer 310, and the additional polymeric layer 350 is disposed over the covering polymeric layer 320 (not shown). In such embodiments, the additional polymeric layer 350 is the intended skin-contacting layer.

As discussed above, for a three or more latex layers condom, in some embodiments, the decorative film, decal, or tattoo 250 can be disposed between any two adjacent latex layers. In other embodiments, the decorative film or tattoo 250 can be disposed such that the decorative film or tattoo 250 contacts only one latex layer. In such embodiments, the decorative film or tattoo 330 is disposed upon the outside surface of the condom, or on the surface of the inside of a condom, i.e., the decorative film or tattoo 250 contacts the skin of a wearer.

Figure 5:
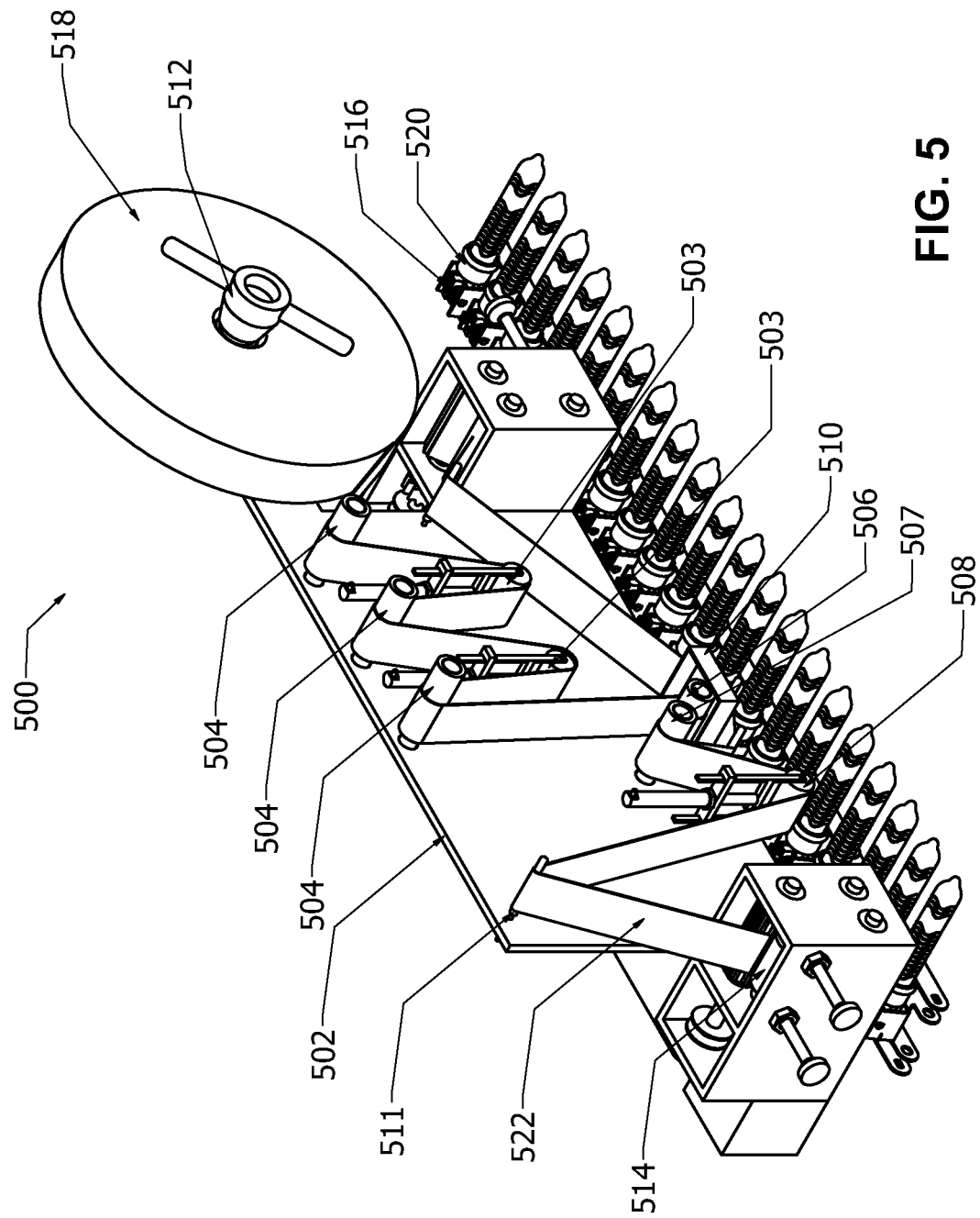
FIG. 5 depicts apparatus for transferring images to polymeric articles, according to embodiments of the invention.

FIG. 5 depicts an apparatus 500 for transferring images to polymeric articles, according to embodiments of the invention. The transfer apparatus 500 comprises a frame 502, which houses a plurality of lower tension rollers 503, a plurality of upper tension rollers 504, a lower bath roller 506, an upper bath roller 507, a fluid bath 510, an upper pin 511, a transfer roller 508, a supply spindle 512, a takeup spindle 514, a plurality of former holders 520, and a conveyor 516. During operation of the apparatus 500, a ribbon roll of decorative images 518, such as a decorative film, decal, or releasable tattoo on a substrate is mounted on the supply spindle 512 and the ribbon roll of images 518 is fed through the plurality of lower tension rollers 503, the plurality of upper tension rollers 504, lower bath roller 506, which is at least partially submerged in the fluid bath 510, the upper bath roller 507, the transfer roller 508, the upper pin 511, which keep a rolling tension on the ribbon roll of images 518, and terminates at the takeup spindle 514. A plurality of former holders 520 are releasably attached to the conveyor 516, which is lower than the fluid bath 510 and the transfer roller 508.

The plurality of former holders 520 have, for example, polymeric condoms or gloves disposed thereon. During operation, the ribbon roll of decorative images 518 travels under lower bath roller 506 through the fluid bath 510, wetting each image and preparing it for release. Thereafter, the ribbon traverses over the upper bath roller 507, down under transfer roller 508, which contacts a polymeric article disposed on one of the plurality of 520, transferring an image, such as a polymeric film, decal, or tattoo onto the polymeric article. The emptied ribbon roll, in other words the substrate, 522 then travels over upper pin 511 and is rolled onto takeup spindle 514. In some embodiments according to the invention, fluid bath 510 has water or another solvent, such as alcohol, or release agent capable of releasing the polymeric film, decal, or tattoo from a substrate. In some embodiments of the invention, the temperature of the fluid bath 510 can be heated up to beyond ambient temperature, for example, to 100° C., to facilitate the ease of transfer the decorative image onto the polymeric article. In yet another embodiment, the transfer roller 508 can also be heated up to beyond ambient temperature to 100° C. to also facilitate the transfer of the image onto the polymeric article, such as a condom or glove.

Embodiments according to the invention include wherein the fluid bath 510 is replaced with a fluid spray station to spray a liquid, such as water or alcohol, on the decorative image before transfer of the decorative image, as opposed to travelling through the fluid batch 510. Embodiments of the invention further comprise a heat source, such as a conductive heater, placed near the transfer roller 508 to heat the decorative film, decal, or tattoo to facilitate release of the decorative image, either alone or in conjunction with the fluid bath 510.

While various embodiments describe, optionally, an application of multiple layers of a polymeric composition, embodiments according to the invention are not limited to layers either for manufacturing or for the manufactured product. Furthermore, the polymeric articles resulting from the manufacturing methods described herein may not include layers, and, in several embodiments, the manufactured article does not include discernible layers. The term "layer" has been used to demonstrate the incremental application of a polymeric composition and positioning of the decorative film relative to the sheath. In other words, an incremental building up of polymeric composition to form a sheath does not necessarily result in demarcated layers of polymeric composition. For example, although the layers may be built up in stages, the sheath resulting therefrom may be integrally formed such that layers formed during such stages are not separable from each other thereafter and thereby form a single layer.

Further, according to embodiments of the invention, each of the covering polymeric layers and the base polymeric layers may comprise the same or different material(s) and/or color(s), or various possible combinations thereof.

While the foregoing is directed to embodiments of the invention, other embodiments of the invention may be devised without departing from the scope thereof, and the scope thereof is determined by the following claims.

What is claimed is:

1. A polymeric condom having a tip configured to fit over a tip of a user's penis, the condom for use by the user in sexual activity with a partner, comprising:
   a polymeric sheath, the sheath comprising at least two tubular polymeric fluid barrier layers that have the shape of the sheath, the sheath having an open end and a closed end at the tip;
   a tubular portion of the sheath corresponding to the tubular polymeric fluid barrier layers; and
   a decoration disposed on a flexible, two-dimensional substrate having a defined area bounded on all sides by edges;
   the two-dimensional substrate conformed to the tubular shape of the polymeric sheath and sandwiched between the at least two tubular polymeric fluid barrier layers, wherein the substrate comprises at least one of a polymeric film, paper, or combination of polymeric film and paper that traverses at least a quarter of a circumference of the at least two tubular polymeric fluid barrier layers, and wherein the decoration comprises an image defined by differences across the image in color or color density.

2. A method for forming the polymeric condom of claim 1, comprising: disposing at least one base polymeric layer of the at least two tubular polymeric fluid barrier layers on a former to form the sheath; applying at least one said decoration; and disposing at least one covering polymeric layer of the at least two tubular polymeric fluid barrier layers onto the at least one base polymeric layer and the at least one decoration, such that the at least one decoration is disposed between the at least one base polymeric layer and the at least one covering polymeric layer.

3. The method of claim 2, wherein the at least one decoration is printed, screen-printed ink-jetted, or laser printed onto the substrate.

4. The method of claim 2, wherein the at least one decoration has a coagulant disposed thereon before being applied onto the at least one base polymeric layer.

5. The method of claim 2, wherein the at least one base polymeric layer on the former is partially dried or allowed to dry before the disposing the at least one covering polymeric layer step.

6. The method of claim 2, further comprising a heating step to at least partially cure the at least one base polymeric layer before the at least one decoration is applied onto the at least one base polymeric layer.

7. The method of claim 2, wherein the at least one decoration is unadorned, and the image is printed, screen-printed, ink-jetted, or laser printed on the substrate after the substrate has been applied to the at least one base polymeric layer and before the at least one covering polymeric layer is disposed thereon.

8. The method of claim 2, further comprising applying a coagulant on the at least one base polymeric layer either before or after the at least one decoration is applied onto the at least one base polymeric layer.

9. The method of claim 2, wherein the at least one decoration is transferred from at least one of a roll or ribbon onto the at least one base polymeric layer.

10. The method of claim 2, wherein disposing the at least one base polymeric layer on the former comprises at least one of spraying a polymeric composition onto the former, or dipping the former in a polymeric composition.

11. The method of claim 2, wherein at least one additional polymeric layer is disposed over the at least one base polymeric layer.

12. The polymeric condom of claim 1, wherein the at least two tubular polymeric fluid barrier layers are: a base polymeric fluid barrier layer and a covering polymeric fluid barrier layer, and wherein a third polymeric fluid barrier layer is disposed on at least one of the base polymeric fluid barrier layer or the covering polymeric fluid barrier layer.

13. The polymeric condom of claim 12, wherein the third polymeric fluid barrier layer is a color different than the base polymeric fluid barrier layer and the covering polymeric fluid barrier layer.

14. The polymeric condom of claim 1, wherein the substrate for the decoration is disposed within the tubular portion of the sheath and not at the sheath tip.

15. The polymeric condom of claim 1, wherein the decoration further comprises at least one of photochromic ink, thermochromic ink, piezochromic ink, photoluminescent ink, fluorescent ink, or glitter disposed on the substrate.

16. The polymeric condom of claim 1, wherein the polymeric sheath is synthetic rubber, natural rubber, polyisoprene, polyurethane, nitriles, carboxylated-nitriles, polychloroprene, a thermoplastic elastomer, or a blend thereof, and wherein the substrate comprises (i) paper, or (ii) combination of polymeric film and paper, or (iii) a polymeric film that is (a) mylar or (b) mylar in further mixture with one or more of acrylic or vinyl.

17. The polymeric condom of claim 1, wherein substrate for the decoration is not coextensive with the sheath.

18. The polymeric condom of claim 1, wherein the at least two tubular polymeric fluid barrier layers are: a base polymeric fluid barrier layer and a covering polymeric fluid barrier layer, and wherein the base polymeric fluid barrier layer is a first color and the covering polymeric fluid barrier layer is a color different than the first color.

19. The polymeric condom of claim 1, wherein the substrate is applied fully formed to one of the tubular polymeric fluid barrier layers prior to being covered by the second tubular polymeric fluid barrier layer.

20. The polymeric article of claim 1, wherein the substrate with decoration is applied to one of the tubular polymeric fluid barrier layers by transfer from a roll or ribbon, and thereafter the second tubular polymeric fluid barrier layer is applied by dipping.

21. The polymeric article of claim 1, wherein the decoration is configured to have a visual impact on the user or the partner.

22. The polymeric article of claim 1, wherein the image is suggestive of a person, animal or other object.

23. The polymeric article of claim 1, wherein the at least two tubular polymeric fluid barrier layers of the same polymeric composition.

24. A polymeric condom having an open end and a closed end, the polymeric condom comprising:
at least two polymeric fluid barrier layers of the same polymeric composition, which form:
a tubular sheath including the open end;
a tip portion extending from the tubular sheath, the tip portion including the closed end;
a decoration sandwiched between the at least two polymeric fluid barrier layers in the tubular sheath and conformed to the shape of the tubular sheath, the decoration comprising: a polymeric film that comprises an acrylic, a mylar, or a vinyl; and an image; and
optionally a ring at the open end.

* * * * *